United States Patent [19]

Chmiel et al.

[11] 4,327,739

[45] May 4, 1982

[54] NONINVASIVE MEASUREMENT OF BLOOD FLOW RATE UTILIZING ULTRASOUND

[76] Inventors: Horst Chmiel, Paracelsusstrasse 14, D-7250 Leonberg; Rudolf Mauser, Haussmannstrasse 146 B, D-7000 Stuttgart 1, both of Fed. Rep. of Germany

[21] Appl. No.: 133,103

[22] Filed: Mar. 24, 1980

[30] Foreign Application Priority Data

Mar. 22, 1979 [DE] Fed. Rep. of Germany ....... 2911258

[51] Int. Cl.³ .............................................. A61B 10/00
[52] U.S. Cl. ................................................... 128/663
[58] Field of Search ....................................... 128/663; 73/861.25–861.29

[56] References Cited

U.S. PATENT DOCUMENTS

| | | | |
|---|---|---|---|
| 3,498,290 | 3/1970 | Shaw et al. | 128/663 |
| 3,605,724 | 9/1971 | Flaherty | 128/661 |
| 3,778,756 | 12/1973 | Houston et al. | 128/661 |
| 3,778,757 | 12/1973 | Houston | 732/626 |
| 3,922,911 | 12/1975 | Groves et al. | 128/663 |
| 4,031,743 | 6/1977 | Kossoff et al. | 367/992 |
| 4,106,492 | 8/1978 | Schoette et al. | 128/661 |
| 4,109,642 | 8/1978 | Reid et al. | 128/663 |

FOREIGN PATENT DOCUMENTS

| | | | |
|---|---|---|---|
| 8517 | 3/1980 | European Pat. Off. | |
| 1907320 | 9/1970 | Fed. Rep. of Germany | 128/663 |
| 4151347 | 4/1973 | Fed. Rep. of Germany | 128/663 |
| 2758039 | 7/1979 | Fed. Rep. of Germany | 128/663 |
| 2159076 | 6/1973 | France | 128/663 |
| 2309865 | 11/1976 | France | 128/660 |
| 1398022 | 6/1975 | United Kingdom | 128/663 |

OTHER PUBLICATIONS

Grossman, H., "Bloodflow Measuring Process" Patentschrift (Deutsche Demokratische Republik) DL 133 040 Nov. 29, 1978.

Primary Examiner—Robert W. Michell
Assistant Examiner—Francis J. Jaworski

[57] ABSTRACT

In order to perform a non-invasive measurement of the blood flow rate in the smallest vessels, i.e. the capillaries, of a blood vessel bed, and to detect the presence of erythrocyte aggregations therein, acoustic pulses containing oscillations at a frequency above 20 MHz are directed through the skin of a subject from a crystal transducer and the resulting echo pulses are processed to produce information based on the Doppler frequency signals relating to blood flow in a predetermined direction and occurring within a time window corresponding to the distance from the crystal of the blood vessels to be examined. Interspersed between the above-mentioned pulses, spike pulses having a duration of the order of 20 ns are similarly transmitted, and echoes thereof are detected for the purpose of detecting the presence of erythrocyte aggregations.

12 Claims, 8 Drawing Figures

NONINVASIVE MEASUREMENT OF BLOOD FLOW RATE UTILIZING ULTRASOUND

BACKGROUND OF THE INVENTION

The present invention relates to an apparatus for the noninvasive measurement of the rate of blood flow according to ultrasonic Doppler effect techniques, the apparatus being of the type which is composed of ultrasonic transmitters and receivers for ultrasonic waves reflected by the flowing blood as well as a device for determining and evaluating the Doppler frequency shift between transmitted and received frequencies.

Such devices are known, one such device being disclosed, for example, in German Offenlegungsschrift [Laid-open Application] No. 2,461,264. These known devices have certain drawbacks, one of which is that they are intended for mesauring the rate of blood flow in relatively large blood vessels. Such devices operate in a frequency range of 5 to 10 MHz since at higher frequencies the attenuation of the ultrasonic waves in body tissue becomes so high that relatively deeply embedded blood vessels can not be monitored. Due to the frequencies employed, it is possible to measure the flow rate in large vessels, where it is of the order of magnitude cm/s, but not flow rates of the order of magnitude of mm/s, or microcirculation, which occur in the smaller blood vessels. Moreover, known devices do not permit differentiation between large and small vessels.

SUMMARY OF THE INVENTION

It is an object of the present invention to monitor the microcirculation, and particularly to detect, for example, a flow rate which increases or decreases with time in all capillary vessels and arterioles of a selected local area when there is practically unchanged flow in the large vessels. A more specific object of the invention is to effect the following:

measurement of low flow rates as in the capillaries with simultaneous suppression of the signals from high flow rates as in the arterioles;

extensive differentiation between the signals from capillaries (a few tenths to 1 mm/s) and arterioles (approximately 1 to 20 mm/s);

evaluation of the changes in time of corpuscle flow (here erythrocyte flow) to thus cover the changes in time in the oxygen carriers which are a prerequisite for oxygen exchange;

detection of erythrocyte aggregations, which occur in the course of the collapse of microcirculation, by means of a delay measurement in the same tissue volume area as the blood flow rate measurement.

This and other objects are achieved, according to the invention, by the provision of novel apparatus for the noninvasive measurement of the blood flow rate in the smallest vessels of a blood vessel system below the skin of a subject and for detection of erythrocyte aggregations in those vessels, utilizing ultrasonic signals, which apparatus includes (a) electroacoustic means for transmitting ultrasonic signals and receiving echoes thereof, these means including a transmitting/receiving crystal;

(b) support means supporting the crystal and arranged to hold the crystal in proximity to the skin and/or other tissue faces such as mucosa and serosa and surfaces of organs such as the liver and kidney of a subject in the region of vessels to be examined and in acoustic signal communication with the skin or face of the tissue or organ of the subject, the support means being arranged to adjustably orient the crystal relative to the skin or face of the tissue or organ for ultrasonic transmission along an axis forming an angle of between 15° and 30° to the skin surface;

(c) first switching means connected for transmitting exciting signals to the crystal for producing ulrasonic energy in the form of successive pulses containing oscillations at a frequency of at least 20 mHz, for measurement of the blood flow rate in such smallest vessels, and spike pulses of a width of the order of 20 ns for detecting erythrocyte aggregations;

(d) second switching means connected to receive and amplify ultrasonic echo signals received by the crystal, for deriving the Doppler frequency components in such signals and for preserving only those Doppler frequency components corresponding to blood flow in a predetermined direction;

(e) comparison means connected for comparing the preserved Doppler frequency components with a selected frequency value corresponding to the maximum flow rate in the smallest vessels under examination; and (f) control means connected to isolate those received signal Doppler frequency components which are received within a predetermined time interval after emission of each ultrasonic pulse by the crystal, corresponding to a predetermined depth range below the skin of the subject and a predetermined measuring volume which is independent of the pulse repetition rate, the control means thereby providing a depth window for the received signals.

The solution provided by the present invention is achieved, in part, by the combination, with various features that are known per se, of a novel electronic depth window with which the signal components of the flow rates in the ends of the flow paths of a selected volume area of body tissue near the surface, i.e. to a depth of about 3 mm, are separated from the components of other areas by taking advantage of the fact that at shallow depths, the greater attenuation occurring at higher frequencies need no longer simply be accepted but can be utilized in a positive sense, the invention thus makes it possible for the first time to measure the flow rate of blood in the smaller vessels and to distinguish this rate from that in the larger vessels. Moreover, it is possible to determine the influence of the hematocrit on the blood flow rate, as well as to periodically, intermittently, i.e. with an effect as if it were done simultaneously, follow the occurrence of erythrocyte aggregations in the same volume area by delay measurements with short, spike, pulses.

Frequency analysis and display in a multichannel analyzer permit semiquantitative characterization of the transport of oxygen carriers. This makes it possible for the first time to objectively determine the success of therapeutic measures, which may, for example, be of a pharmacologic or physical nature. An important field of use for the present invention is hemodilution which must be practiced today in intensive care facilities where controls cannot be maintained. The present invention makes it possible for the first time to optimize hemodilution in antishock therapy.

The actual purpose of the physiological circulatory system is to exchange matter between blood and tissue, which takes place in the area of the smallest vessesls—the so-called end of the flow path or microcirculation. Since microcirculation must be considered as a functional and thus life-supporting event its detection and monitoring are of great medical importance.

The arterioles emanating from small arteries have walls along which extend a very large number of smooth muscles so that the arterioles are capable, by significantly contracting these muscles, of varying the flow resistance and even of closing down completely.

With respect to the arrangement of the vessels relative to one another, there exist such organ-specific differences that generalization is impossible. Yet the nutrient capillaries are provided in large numbers and extend mainly parallel to the so-called major flow channels. From the arerioles spring metarterioles which are also associated with muscles, and from these emanate capillaries. However, capillaries may also emanate directly from the arterioles.

The walls of the capillaries consist of a thin layer of endothelial cells having basal membranes which permit metabolism between the blood within the capillaries and the interstitial fluid surrounding the tissue cells. Metabolism is aided by small diameter and with the larger number and density of the capillary vessels, but certain problems are encountered by the circulating blood.

While the large vessels carrying fast flowing blood optimally adapt themselves to these conditions, there exists the danger with a slow flow of clogging the narrowest nutrient capillaries by blood components or by endothelial swelling. After flowing through the capillaries, the blood flows through venules, which themselves are branches of the large veins, into the right auricle of the heart. While the average pressure in the small arteries still lies between 70-100 mm Hg, there occurs a steep pressure drop in the arterioles so that at the beginning of the capillaries the pressure is about 30 mm Hg and at their ends the pressure is only about 12-20 mm Hg. Pulsating flow and such a pressure can still be detected in the arterioles and in the beginnings of the capillaries, but no longer in their further reaches.

Since the inner diameter of the blood capillaries may be smaller than the diameters of the blood corpuscles, the latter can be usually pass only in a deformed state. The deformability of the erythrocytes depends, inter alia, on the effective viscosity and the still not completely explained interaction between capillary wall surface and blood corpuscle surface which improves slidability. In some of the peripheral areas of the circulatory system, for example, in an extremity, there usually occur nonlinearities between the relationship of flow pressure and flow intensity. These result in part from the rheologic properties of the blood, but mainly from the resistance behavior of the vessels. If the contraction state of the smooth muscles of the arterioles remains constant, the arterioles and capillaries will widen with increasing flow pressure, and flow resistance will be reduced. At the same time flow intensity increases over-proportionally with increasing flow pressure.

If the flow pressure is reduced in the lower region of the intensity-pressure (I-P) relationship, the flow stops already at a point in time when the flow pressure is still greater than zero. The reason for this is mainly that the active tension of the smooth muscles, which leads to constriction of the vessel, is higher now than the effect of the transmural pressure which expands the vessel. If a certain critical closing pressure is no longer present, the vessel collapses. Most of the individual partial regions and organs automatically adapt their blood supply to changing requirements in that local metabolism products, i.e. metabolites, reduce the contraction state of the smooth muscles or the arterioles and thus also reduce the local flow resistance. The resulting increased blood supply causes a reduction in concentration of the metabolites so that the blood supply, which equals the quantity of blood flowing through, drops again. These local occurrences have the characteristics typical of a control path whose closed circuit is provided with a feedback loop.

When there are acute hemodynamic malfunctions, such as occurs, for example, from shock, the capillary blood supply is reduced to such an extent that hypoxia (lack of oxygen in the tissues) develops, which results in functional and morphological changes.

In every case of grave shock, thromboplastic (coagulant) material is released within a very short period. This leads in to agglutination of thrombocytes (platelets) and as a consequence to erythrocyte aggregation, i.e. accumulation of red blood corpuscles.

With a steadily increasing erythrocyte aggregation, an albumin-globulin relationship in favor of higher molecular globulins produces an increase in viscosity (reduced elasticity and blood sludge).

The reduced viscosity of the blood leads to erythrostasis (stoppage of red blood corpuscles) with clogging of the venules (small venous vessels) and capillaries (minute blood vessels). Due to a drop in blood pressure and constriction of the arterioles, the flow rate in the capillary region is reduced considerably so that microcirculation stops. The resulting hypoxia (reduced breathing of the cells due to reduced oxygen pressure) leads, via tissue acidosis (increase in acidity) and local metabolic damage, to serious impairment of the entire organism.

DESCRIPTION OF THE PREFERRED EMBODIMENTS

Figure 1B:
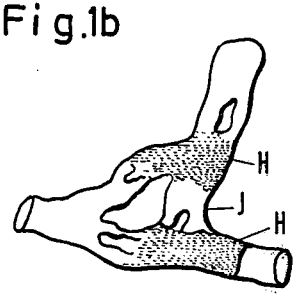
FIG. 1b is a view of the same portion as FIG. 1a, but depicting the condition present in the case of a state of shock.
Figure 1:
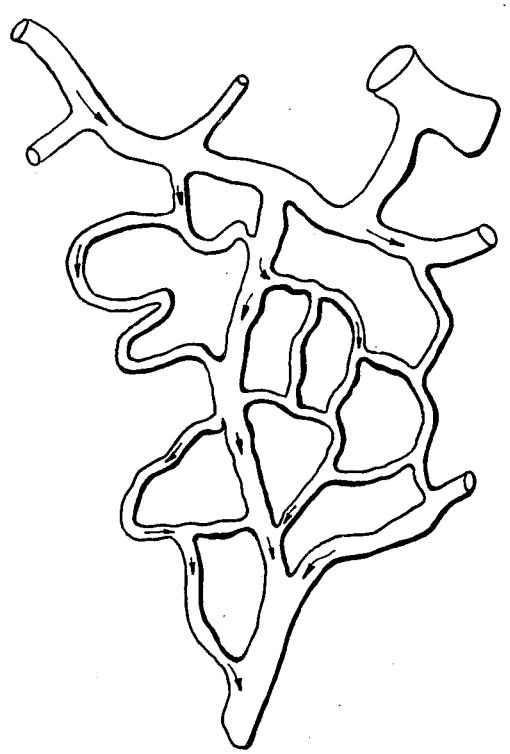
FIG. 1 is a schematic pictorial view of a part of a capillary bed within a human.
Figure 1A:
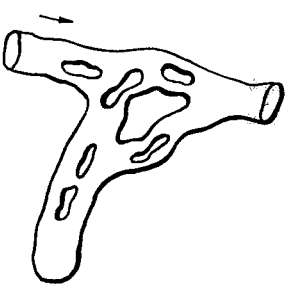
FIG. 1a is an enlarged detail view of the portion of the structure of FIG. 1 in a normal condition.

FIG. 1 is a schematic representation of part of a capillary bed while FIGS. 1a and 1b are enlarged views of the portion of the bed enclosed by a circle in FIG. 1. While FIG. 1a depicts normal erythrocyte movement, FIG. 1b illustrates the shock state which is characterized by erythrocyte aggregations H and plasma inclusions J. The diameter of the illustrated vessels lies between 6 and 40μ (capillaries and arterioles) with a wall thickness of between 1 and 20μ.

In order to cover a maximum shift frequency, or Doppler frequency, Δf of the blood flow rate, which in the ends of the flow paths is about 1 mm/s, ultrasonic frequencies of at least 20 MHz are here required for measurement of the blood flow rate and narrow pulses of a width of, e.g., 20 ns are necessary for detection of an aggregation.

Figure 2:
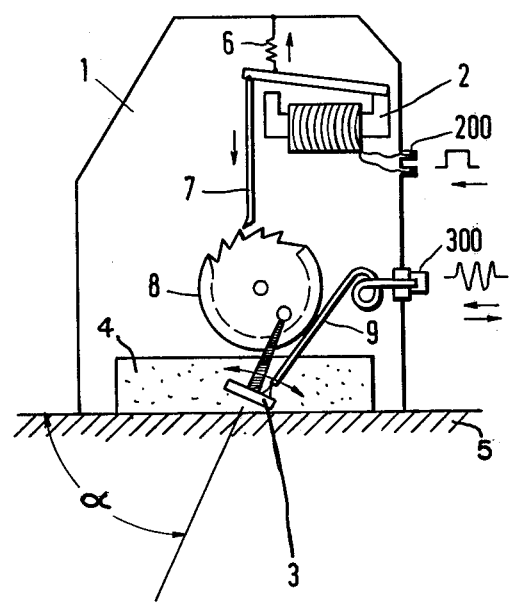
FIG. 2 is a pictorial, elevational view of an ultrasonic transmitting/receiving device according to the invention.

For this purpose, as shown in FIG. 2, a piezocrystal 3 of lead zirconate titanate or other equivalent crystalline or amorphous material of a size of about 1 mm$^2$ is placed at the location to be examined, with a transmission path filled with an acoustic coupling gel 4 interposed between crystal 3 and the associated body surfaces 5. The transmitting/receiving crystal 3 is disposed in a holding device 1 and is positioned by a microstepping motor 2 in such a manner that a sonic angle displacement of the crystal is between 15° to 30° with respect to the body surface 5 (i.e., skin or face of the tissue or organ being examined), can be performed in steps of 1° each. For this purpose the stepping motor (2) has a pawl element (7) under the force of a pull spring (6). The pawl element is meshed with a drive wheel (8). A rod (9) is excentrically and rigidly fixed to the drive wheel and carries the crystal (3) on its free end. The electrical contact for the crystal is provided by a highly flexible wire (9) which ends at an RF 300 connector. A 200 connector serves to supply the control impulses for the stepping motor (2).

With this device it becomes possible to substantially eliminate a falsification corresponding to the actual velocity relationships as a result of an unfavorable position of the transmitting/receiving crystal 3 with respect to the vessel bed and the resulting detection of flow rate components from larger vessels. In the normal case, the sound is radiated in at an angle of 15° to the body surface 5. However, this may have the result that sonic energy impinges laterally on a larger blood vessel in such a manner that a flow rate is detected which does not correspond to the actual rate in the capillaries. By changing the angular position of the transmitting-/receiving crystal 3 via the stepping motor 2, which is achieved by applying one or more pulses to the motor, and/or by shifting the holding device 1, this interference factor is eliminated. Control of the crystal orientation can be effected by comparing the received Doppler frequency with a given value, as will now be explained with reference to FIG. 3.

Figure 3:
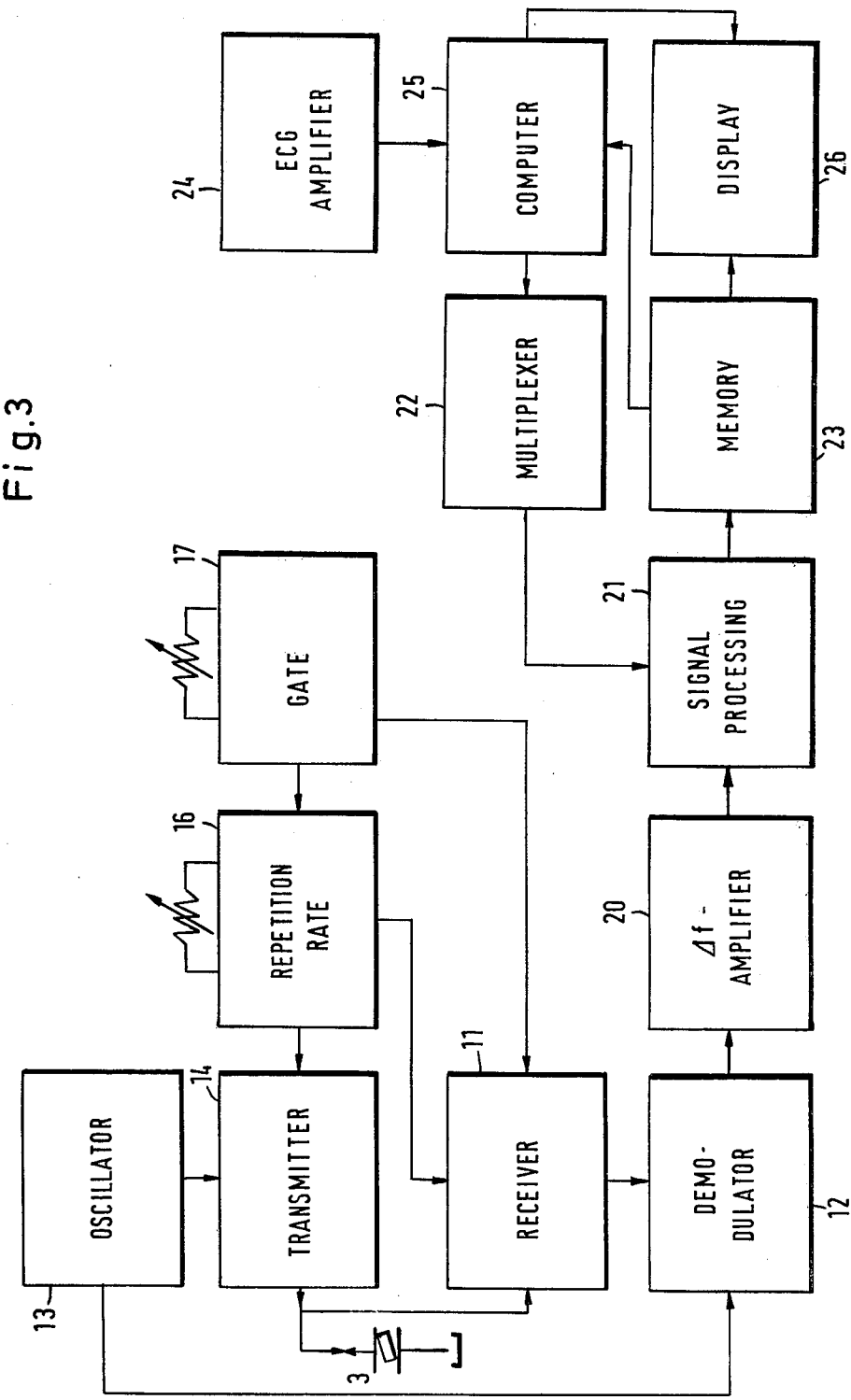
FIG. 3 is a block diagram of one preferred embodiment of the invention.

FIG. 3 is a block circuit diagram of a preferred embodiment of transmitting and receiving circuitry for measuring blood flow rate. The stepping motor 2 of FIG. 2 is controlled in that a given frequency value is applied to a comparison stage of a receiver 11 and this frequency is compared with the Doppler frequency Δf received from crystal 3. If Δf is higher than the given frequency value, the stepping motor is controlled until Δf becomes equal to or less than the given frequency. The given frequency can be given a value at least equal to the Doppler frequency that would be produced by the highest flow rate which could exist in the vessels of interest.

Since in the vessel regions relevant from a medical point of view there exists principally only one direction of flow i.e. from the arterial to the venous side, but a simulated "return flow" is also registered in the form of a negative Δf from vessels oriented in a transverse or opposite direction, further processing involves demodulation in a demodulator 12 of only the frequencies with positive sign, corresponding to those blood vessels supporting a flow toward the transmitting/receiving crystal.

Figure 4:
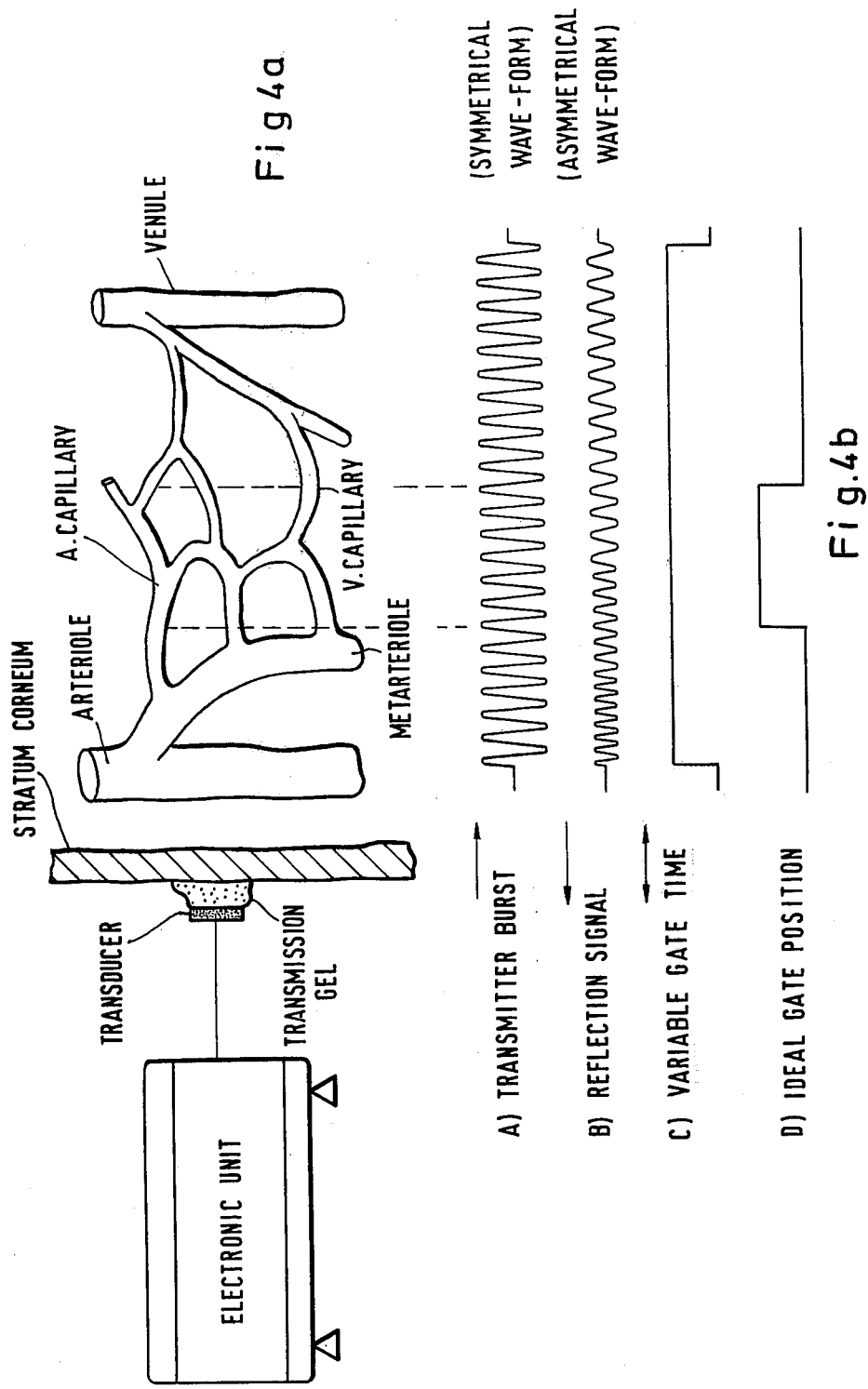
FIG. 4a is a partly schematic, partly pictorial view of a blood vessel system and ultrasonic measuring device.
FIG. 4b is a diagram illustrating the operation of the arrangement of FIG. 4a according to the invention.

FIG. 4a is a pictorial representation of a portion of a blood vessel system below the skin, with an ultrasonic transducer applied to the skin via a mass of transmission gel and connected to an electronic unit for bidirectional conduction of ultrasonic signals. The blood vessel system includes arterioles close to the body surface and venules therebetween. Communicating between the arterioles and venules there are disposed, in succession, metarterioles, arterial capillaries and veinal capillaries. The region bounded by vertical broken lines is characterized by the absence of larger vessels.

In FIG. 4b waveform A shows the waveform of one transmitted pulse and waveform B the resulting echo signal from the vessel bed shown in FIG. 4a. Waveform C represents the available width of the electronic gate, the ideal time position and width of which is shown by waveform D. The ideal position and width correspond to the time of receipt of echoes from the portion of the vessel bed bounded by the broken lines of FIG. 4a, where larger vessels are not present. The width of the gate represented by waveform B can be set digitally in stages of 0.001 mm independently of its position and can be expanded to the length of the transmitted pulse minus the first wave cycles or zero passages, respectively of the echo signal, which correspond to the transient times of the transmitting/receiving crystal and of the associated amplifier.

FIG. 3 already referred to above, is a greatly simplified circuit diagram for a measuring device according to the invention for measuring the blood flow rate. An oscillator 13 generates an oscillation at a high frequency which coresponds to the resonant frequency of the transmitting/receiving crystal and which is applied to this crystal via a transmitter 14 which is caused to operate in a pulsed manner. The duration and repetition rate of each of the pulses set via a repetition rate unit 16 to be continuous and reproducible in a ratio of 1:1 to 1:16. Unit 16 is controlled by a gate member 17 and is connected to receiver 11 to cause the transmitting/receiving crystal to be switched from transmitting to receiving during the intervals between pulses. The echo received by the receiver during the same pulse period as the transmitted signal is limited in time by the set gate width, corresponding to the depth of the tissues of interest, controlled by gate 17 and is fed to demodulator 12 which is synchronized by the oscillator. The length of the transmitted and rceived pulse packages, which corresponds to the depth of the tissue in question, is set by the gate (17). See also the description to FIG. 4b. The demodulator (12) compares the high frequency supplied by the oscillator (13) with the modulated high frequency received through the blood flow and forms the difference frequency Δf by FM-demodulation. An integrated circuit of the type ML 1596 (MOTOROLA) is used as an FM demodulator.

After separating out the high frequency components and any negative Δf associated with a simulated "return flow", the remaining signal is amplified and filtered through a lowpass, Δf filter and amplifier 20.

Signal components at the frequency Δf in the range of 1 to 1000 Hz, proportional to the flow rate, are intermediately stored in a subsequent signal processing unit 21 and are subdivided into narrowband frequency channels which are interrogated by a computer controlled multiplexer 22 and are summed and stored in a memory 23.

The Δf (audio) signal put out by the amplifier (20) and which corresponds to the blood flow rate is digitalized in the signal processing unit (21), buffered, and, as mentioned above, divided up into narrow-band frequency channels (for example, of 10 Hz each). The signal processing unit (21) can be an integrated circuit for the type 8702 (Teledyne) which contains an analog/digital converter.

Under the control of the multiplexer (22) the frequencies (channels) occurring at different times within the length of a received pulse package are transmitted by channel in a sequence of, for example, 1 to 1,000 Hz to the memory (23) and stored in digital form. The computer (25) sees to it that the frequency segments are added. The storage (23) can be, example, an integrated circuit of the type NS 3000-1 (National Semiconductor) with a storage capacity of at least 16 kBit. A suitable multiplexer (22) is a cascaded integrated circuit of the type CD 4051 (RCA). in this time interval. This has the advantage, inter alia, that the extremely high sensitivity of the measuring device cuts out all interference signals between two systoles and only the occurrences during the diastole are evaluated which are of interest for the physician.

This device additionally makes it possible to recognize a premature contraction (extrasystole) in the flow rate histogram, inasmuch as it manifests itself in the periphery, and to clearly distinguish it from respiratory changes.

In this connection periphery means the acral points of the extremities.

Figure 5:
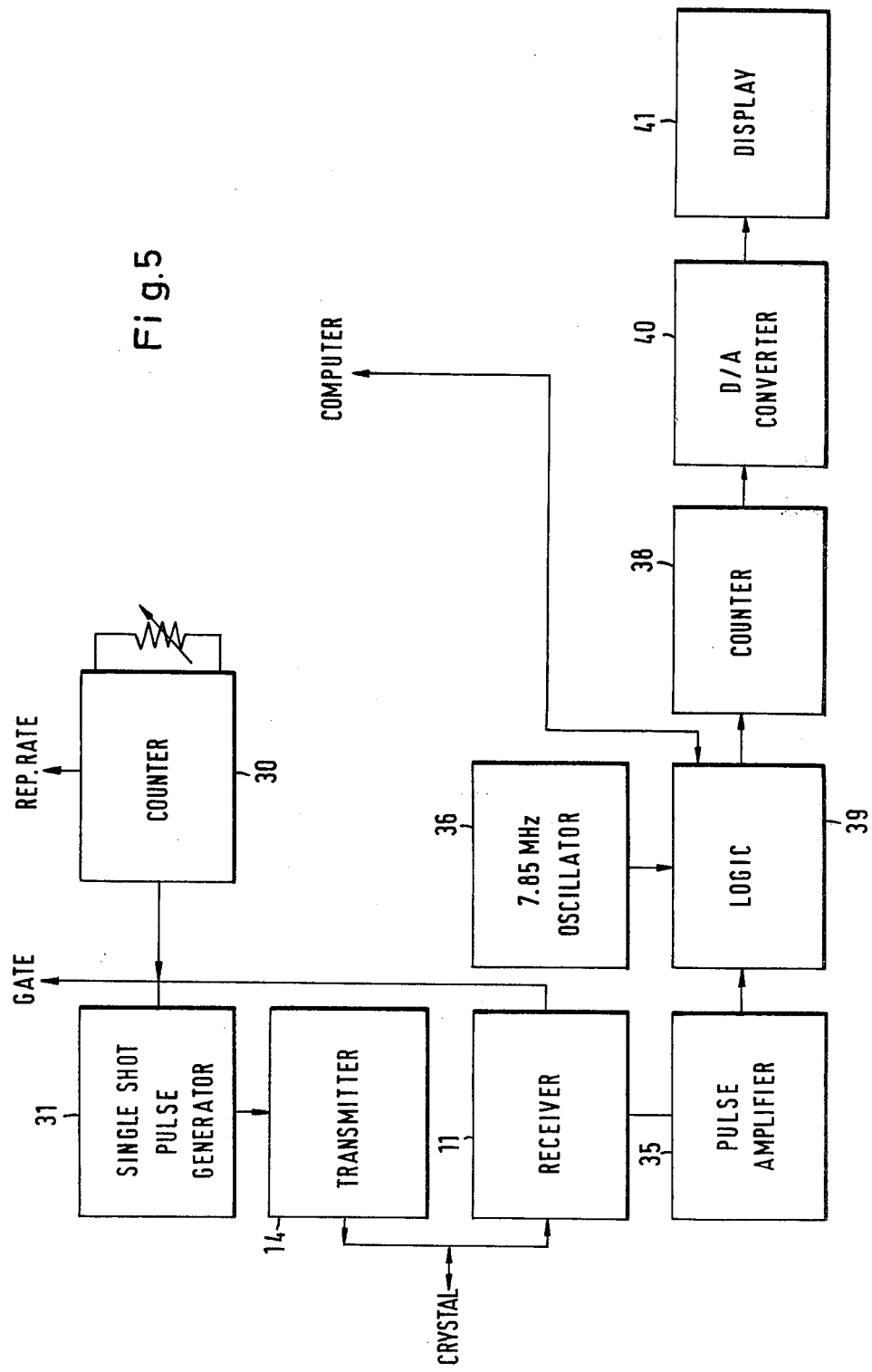
FIG. 5 is a block circuit diagram of a further measuring system according to the invention.

After every $n^{th}$ transmitting pulse where, e.g. n=5000, for measuring the blood flow rate, a pulse travel time measurement is made with the same transmitting/receiving crystal to detect erythrocyte aggregations. The circuit arrangement shown in FIG. 5 is employed for this purpose.

A preselection counter 30 controlled by the repetition rate unit 16 of FIG. 3 controls transmitter 14 via a single shot pulse generator 21 to apply to the transmitting/receiving crystal individual spike pulses, e.g. individual sinusoidal halfwaves, corresponding to the resonant frequency of the crystal. At the occurrence of an erythrocyte aggregation in the set gate region an echo will appear which is fed via receiver 11 to a pulse amplifier 35.

Corresponding to a speed of a sound of 1570 m/s for the ultrasonic waves in blood and tissue, a quartz oscillator 36 operating at a selected fixed frequency, e.g. 7.85 MHz, corresponding to half the speed of sound, is used as a counting pulse signal generator for the travel time measurement.

With the emission of a transmitting pulse the, e.g. 7.85 MHz, signal is switched to a counter 38 via logic 39 and is stopped when an echo arrives. The indicated digital measuring result corresponds directly to the depth of the erythrocyte aggregation. After D/A conversion in a converter 40 the result is displayed in analog form in a display 41 to indicate the movement of the aggregation.

Since the detection of an aggregation leads to a drastic change in the blood flow rate (drop and/or rise) the curves of such occurrence can be correlated on the two channels, shown in 4 and 5, of the display and thus the physician can take timely preventive measures and, under certain circumstances prevent the onset of shock.

If no aggregation is detected by means of the delay device of FIG. 5, the counter 38 erases itself after a predetermined time and remains ready to receive the next transmitted pulse.

The repetition rate unit (16) consists mainly of two monostable multivibrators made of common integrated circuits. These two multivibrators have a mutual influence on each other in that the metastable time of the first multivibrator determines the length of the pulse package, while that of the second multivibrator determines the length of the pause between two pulse packages. Their times are best determined by variable RC-components.

The display (26) is either a conventional chart recorder and/or a storage monitor (tv) which records the blood flow as a function of time.

The preselection counter (30) is a digital binary counter of the type MC 14040 (MOTOROLA), for 4096 bits. According to how it has been preset the preselection counter sends a trigger impulse to the single shot pulse generator (31) after even n-th impulse package.

The D/A converter (40), for example of the type DAC-04, 10 bit (Precision Monolithics), converts the digital information of the counter (38) into an analog curve from which appears on the display (41). The display (41) can be of the same type as the display (26) in FIG. 3.

The repetition rate unit (16) blocks the receiver (11) during the time when an impulse package is switched on the crystal (3) (compare FIG. 3) and opens the receiver after the transmission phase has been ended. The window region (compare FIG. 46, position D) relevant to the blood flow being examined is chosen by means of the gate (17) from the incoming echo, the length of which corresponds to the transmission impulse package.

The computer (25) is a CBM 3032, with a V 24 interface (manufactured by Commodore).

It will be understood that the above description of the present invention is susceptible to various modifications, changes and adaptations, and the same are intended to be comprehended within the meaning and range of equivalents of the appended claims.

What is claimed is:

1. Apparatus for the noninvasive measurement of the blood flow rate in the smallest vessels of a blood vessel system below the skin of a subject and for detection of erythrocyte aggregations in those vessels, utilizing ultrasonic signals, said apparatus comprising:

(a) electroacoustic means for transmitting ultrasonic signals and receiving echoes thereof, said means including a transmitting/receiving crystal;
   (b) support means supporting said crystal and arranged to hold said crystal in proximity to the skin of a subject in the region of vessels to be examined and in acoustic signal communication with the skin of the subject, said support means being arranged to adjustably orient said crystal relative to the skin for ultrasonic transmission along an axis forming an angle of between 15° and 30° to the skin surface;
   (c) first switching means connected for transmitting exciting signals to said crystal for producing ultrasonic energy in the form of successive pulses containing oscillations at a frequency of at least 20 MHz, for measurement of the blood flow rate in such smallest vessels, and spike pulses of a width of the order of 20 ns for detecting erythrocyte aggregations;

(d) second switching means connected to receive and amplify ultrasonic echo signals received by said crystal, for deriving the Doppler frequency components in such signals and for preserving only those Doppler frequency components corresponding to blood flow in a predetermined direction;

(e) comparison means connected for comparing the preserved Doppler frequency components with a selected frequency value corresponding to the maximum flow rate in the smallest vessels under examination; and (f) control means connected to isolate those received signal Doppler frequency components which are received within a predetermined time interval after emission of each ultrasonic pulse by said crystal, corresponding to a predetermined depth range below the skin of the subject and a predetermined measuring volume which is independent of the pulse repetition rate, said control means thereby providing a depth window for the received signals.

2. An arrangement as defined in claim 1 wherein said support means comprise positioning means for automatically adjusting the orientation of said crystal.

3. An arrangement as defined in claim 2 wherein said positioning means comprise a stepping motor.

4. An arrangement as defined in claim 2 wherein said control means comprise a counting device connected for electronically suppressing a portion of an echo pulse signal received by said crystal associated with the first zero passages of that signal, for thereby eliminating spurious Doppler frequency indications produced during the starting transient period associated with each ultrasonic signal pulse.

5. An arrangement as defined in claim 4 wherein said first switching means comprise adjusting means connected for setting the duration of each of the successive pulses, to thereby control the emitted power an ultrasonic energy penetration depth.

6. An arrangement as defined in claim 5 wherein said support means are arranged for establishing an acoustic signal transmission path between said crystal and the subject's skin, and other tissue faces such as mucosa and serosa and surfaces of organs such as liver and kidney.

7. An arrangement as defined in claim 6 wherein said adjusting means are arranged to set the repetition rate of said successive pulses independently of the length and position of the depth window provided by said control means.

8. An arrangement as defined in claim 7 wherein said second switching means comprise actuating means connected to receive a separately derived ECG systole signal and to actuate a predetermined, delayed echo signal evaluation interval dependent on that ECG signal.

9. An arrangement as defined in claim 7 wherein said second switching means further comprises frequency analyzing means connected for separating the received Doppler frequency signal components on the basis of the direction of blood flow in the vessels being examined and for summing individual frequency components thereof in order to produce a frequency spectrum display corresponding to the actual flow rate pattern existing in the vessels being examined.

10. An arrangement as defined in claim 9 wherein said first switching means comprise a control element connected for emitting a spike pulse after each occurrence of a selected number of said successive pulses, which number is selected independently of the parameters of said successive pulses.

11. An arrangement as defined in claim 9 wherin said frequency analyzing means comprises an electronic evaluation device connected for processing the derived frequency spectrum information in such a manner as to permit evaluation of changes in erythrocyte flow.

12. An arrangement as defined in claim 11 wherein the results produced by said electronic evaluation device are used for optimizing hemodilution.

* * * * *

UNITED STATES PATENT AND TRADEMARK OFFICE
CERTIFICATE OF CORRECTION

PATENT NO. : 4,627,739
DATED : December 9 , 1986
INVENTOR(S) : Shingo ICHIKAWA ET AL.

It is certified that error appears in the above-identified patent and that said Letters Patent is hereby corrected as shown below:

Title page:

Line "[75] Inventors: Ichikawa Shingo; Hisahide" should be

-- [75] Inventors: Shingo Ichikawa; Hisahide --.

Signed and Sealed this

Tenth Day of March, 1987

Attest:

Attesting Officer

DONALD J. QUIGG

Commissioner of Patents and Trademarks